United States Patent [19]

Colville

[11] 4,257,405

[45] Mar. 24, 1981

[54] BONE GRAFT MATERIALS

[76] Inventor: James Colville, Foxrock Co. Dublin, Eire, Ireland

[21] Appl. No.: 9,896

[22] Filed: Feb. 6, 1979

[51] Int. Cl.$^3$ .............................................. A61B 19/00
[52] U.S. Cl. ........................................... 128/1 R; 3/1
[58] Field of Search .................. 128/92 C, 92 G, 1 R; 3/1, 1.9

[56] References Cited

U.S. PATENT DOCUMENTS

| | | | |
|---|---|---|---|
| 3,526,906 | 9/1970 | De Laszlo | 3/1.5 |
| 3,623,164 | 11/1971 | Bokros | 3/1.9 |
| 3,707,006 | 12/1972 | Bokros | 3/1.9 |

FOREIGN PATENT DOCUMENTS 2628624  1/1977  Fed. Rep. of Germany ............ 3/1.913

OTHER PUBLICATIONS

"Typical Average Properties of Graphite & Carbon" *Chem. Engr. Handbook*, Perry & Chilton, McGraw Hill, 1973, pp. 23-68 and 23-69.

*Primary Examiner*—Robert W. Michell
*Assistant Examiner*—T. J. Wallen
*Attorney, Agent, or Firm*—Steele, Gould & Fried

[57] ABSTRACT

A bone graft material, especially for repairing skeletal defects, formed of carbonized wood; best results have been achieved with carbonized stemwoods of climbing plants, e.g. Clematis, which have the most advantageous pore size and porosity to accept bone ingrowth upon implantation.

2 Claims, No Drawings

BONE GRAFT MATERIALS

BACKGROUND OF THE INVENTION

This invention relates to bone graft materials.

Bone grafting is a common procedure in orthopaedic practice. There is little doubt that at present the most effective osseous graft material available is fresh autologous bone. However the source of supply is limited and in most cases an additional surgical exposure is necessary to obtain the graft. The use of foreign material (implant) has therefore advantages for both patient and surgeon. Many types of foreign material have been suggested in the past.

Porous materials have been shown to allow the ingrowth of living tissue and this fact is made use of in clinical situations. For example polyester or polytetrafluoroethylene weaves are used to replace blood vessels. At present, porous ceramics and rigid polymers are being tested in an attempt to attach artificial teeth to the alveolar ridge.

Excellent biocompatibility has been demonstrated in various animals to vitreous carbon (Kenner et al., J. Biomed. Mat. Res. 9 111), graphite filaments reinforced with epoxy resins (Musikant, J. Biomed. Mat. Res. 1 225), powdered carbon (Bechtol et al., "Metals and Engineering in Bone and Joint Surgery", Williams and Wilkins, Baltimore, 1959), porous carbon (Stanitski et al., Clemson University Symposium, Clemson S.C., U.S.A. 1972), and solid carbon (Mooney et al., J. Biomed. Mat. Res. 5 143). Recently, filamentary carbon developed from polyacrylonitrile and developed at the Royal Aircraft Establishment, Farnborough, U.K. has been used to repair tendons in rabbits and sheep (Jenkins et al., J. Bone & Joint Surgery, 59B, No. 1, 53).

The use of porous implants in orthopaedics has been almost exclusively directed to the aim of achieving permanent attachment of prostheses to bone, thus most work has been conducted with high strength materials (e.g. porous ceramics or metals). Research into porous carbon has been conducted (e.g. Cestero et al., J. Biomed. Mat. Res., Symposium No. 6, 1, 1975), but the aim has also been to attach material or prostheses to bone.

The known carbon implants arise from synthetic forms of carbon. Moreover, there appears to have been no previous thought given to the use of a porous implant to repair a skeletal defect (thus acting as a bone substitute). I have considered that implants prepared from a natural source of carbon may have advantages over these known synthetic forms, and especially for skeletal defect repair.

SUMMARY OF THE INVENTION

Wood can be reduced to pure carbon and, in addition, is naturally porous. I have discovered that such carbonised wood has excellent tissue biocompatibility and the porosity which can be achieved makes such material an excellent candidate for use in bone grafting. In accordance with the present invention I provide a bone graft material comprised of carbonised wood.

DESCRIPTION OF THE PREFERRED EMBODIMENT

Stem wood is composed of wood fibres and vessels, the former for support and the latter for transport of sap from roots to leaves. In addition, cellular elements in the parenchyma provide storage and mobilising substance, e.g. starch. Vessel diameters vary according to species, climate and time of year. For example, in temperate climates vessels of spring wood are larger than those of autumn wood—where growth has almost ceased.

The greater part of the cell wall of wood is cellulose. It is capable of undergoing thermal decomposition, without the presence of a melting stage, to form a carbonaceous residue. It is this carbonaceous residue of various types of wood which I have discovered is a suitable bone graft material. Not only does such material have good tissue biocompatibility, but there is also some evidence to show that it may gradually become absorbed by the body as the fresh bone grows into the pores of the grafted material.

The actual carbonisation process for wood whereby to provide a pure porous carbonaceous residue is well-known, for example see Gill, "Carbon Fibres in Composite Materials" published for the Plastics Institute, London Life Books (1972), p22. It consists essentially of heating pieces of wood to about 700° C. or higher for several hours in an inert atmosphere. Although there is considerable weight loss and some shrinkage, essentially the pore structure of the wood remains after carbonisation.

Several different types of wood have been carbonised and then tested by me as bone graft materials. Although all have shown good tissue biocompatibility, some have proved more receptive to the ingrowth of bone and this can be explained by the difference in porosity in the samples. The average pore diameter of the wood to be carbonised should be sufficient to encourage healthy bone ingrowth. Typically it will be at least about 30 microns, more preferably at least about 50 microns and advantageously at least about 100 microns. A maximum upper limit of about 500 microns is preferred (above which bone ingrowth becomes reduced). In order to provide sufficient number of these pores of appropriate diameter, the porosity of the wood should be high, preferably at least 20%, more preferably at least 30% and advantageously at least 50% of the total volume. These values are essentially maintained upon carbonisation.

Although probably many woods have the pore size/porosity characteristics to make them suitable candidates, when carbonised, for bone graft materials, I have found that of the woods I have tested, those of rapid climbing plants are the best. Of these, I have achieved greatest success with carbonised specimens of *Clematis Vitalba L.* (and to a lesser extent *Parthenocissus tricuspidata L.*, which is a vine). Stem wood from these plants has an average pore diameter of 150 to 400 microns and a porosity of 50 to 70% total volume.

For use by surgeons as an implant material, the wood after carbonisation must be sterilised prior to use. It may, for example, be sterilised and packed in sterile form for storage and subsequent use in the operating theatre.

EXAMPLE

Samples of the stem wood of *Clematis Vitalba L.* and *Parthenocissus tricuspidata L.* were cut into small pieces approximately 3 mm$^2$ and placed in a vertical furnace, inside diameter 5 cms and length 8 cms. Nitrogen gas was passed through the furnace at a rate of 5 liters/minute (at normal pressure) for one hour before heating began (this ensured the exclusion of oxygen and prevented combustion). The temperature was then raised to 850° C. and kept constant for five hours. The samples were allowed to cool in the inert atmosphere before removal from the oven. They were then autoclaved prior to implantation in rabbits.

Implantation was made in each iliac bone and in the greater trochanter of a group of rabbits and the wounds closed and dressed. At various intervals the rabbits were sacrificed and the implant and surrounding bone removed for inspection. After about 40 days no foreign body reaction to the carbon could be detected and bone ingrowth into the implants had occurred. The best results were obtained with the Clematis samples, where bone was discovered growing diffusly right through the specimen implants.

I claim:

1. A method of repairing a skeletal defect in the body, which comprises grafting a bone graft material into the defect, said material being carbonised wood, having a porosity of at least 30% total volume and an average pore diameter of at least 30 microns, whereby said material is absorbed by the body after grafting, being replaced by fresh bone growth.

2. A method for repairing a sketetal defect in the body, which comprises grafting bone graft material into the defect, said material consisting essentially of pure carbon formed by carbonizing wood in an inert atmosphere, said carbon having a porosity of at least 30% total volume and an average pore diameter of at least 30 microns, whereby said material is absorbed by the body after grafting, being replaced by fresh bone growth.

* * * * *